United States Patent
Hewitt

(10) Patent No.: US 11,872,297 B2
(45) Date of Patent: Jan. 16, 2024

(54) ANTI-ACNE COMPOSITION

(71) Applicant: Advance NanoTek Ltd., Rocklea (AU)

(72) Inventor: Julian Hewitt, Durham (GB)

(73) Assignee: Advance Zinctek Limited, Queensland (AU)

( * ) Notice: Subject to any disclaimer, the term of this patent is extended or adjusted under 35 U.S.C. 154(b) by 0 days.

(21) Appl. No.: 17/290,165

(22) PCT Filed: Oct. 30, 2019

(86) PCT No.: PCT/AU2019/051195
§ 371 (c)(1),
(2) Date: Apr. 29, 2021

(87) PCT Pub. No.: WO2020/087121
PCT Pub. Date: May 7, 2020

(65) Prior Publication Data
US 2022/0000735 A1    Jan. 6, 2022

(30) Foreign Application Priority Data
Oct. 30, 2018  (AU) ................................ 2018904114

(51) Int. Cl.
| | |
|---|---|
| *A61K 8/368* | (2006.01) |
| *A61K 8/9789* | (2017.01) |
| *A61K 8/27* | (2006.01) |
| *A61Q 17/04* | (2006.01) |
| *A61Q 19/00* | (2006.01) |

(52) U.S. Cl.
CPC ................ *A61K 8/368* (2013.01); *A61K 8/27* (2013.01); *A61K 8/9789* (2017.08); *A61Q 17/04* (2013.01); *A61Q 19/00* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 7,390,355 | B2 | 6/2008 | Lyth |
| 2003/0202948 | A1 | 10/2003 | Koini et al. |
| 2006/0228310 | A1 | 10/2006 | Lyth |
| 2008/0057008 | A1 | 3/2008 | Naden et al. |
| 2008/0233060 | A1 | 9/2008 | Grune |
| 2010/0143426 | A1 | 6/2010 | Laba |
| 2010/0310871 | A1 | 12/2010 | McCormick et al. |
| 2010/0316582 | A1 | 12/2010 | Tsuzuki |
| 2012/0107253 | A1 | 5/2012 | Xing et al. |
| 2012/0263661 | A1 | 10/2012 | Grune |
| 2014/0255323 | A1 | 9/2014 | Ishida et al. |
| 2016/0120781 | A1* | 5/2016 | Powell .................... A61P 43/00 424/617 |
| 2016/0200457 | A1 | 8/2016 | Yamaguchi et al. |
| 2020/0214952 | A1* | 7/2020 | Chandler ............. A61K 8/0275 |

FOREIGN PATENT DOCUMENTS

| | | | |
|---|---|---|---|
| CN | 102871850 A | 1/2013 | |
| DE | 102004004969 A1 | 8/2005 | |
| JP | 2012-201660 A | 10/2012 | |
| JP | 2018-154613 A | 10/2018 | |
| WO | WO-9321899 A1 * | 11/1993 | ............. A61K 31/60 |
| WO | WO2007/117352 A2 | 10/2007 | |
| WO | WO 2009/089523 A1 | 7/2009 | |
| WO | WO 2010/077971 A2 | 7/2010 | |

OTHER PUBLICATIONS

Honest Beauty Review, Retrieved from URL: https://beautywithinandout.wordpress.com/2016/05/19/honest-beauty-review/, May 19, 2016 (Year: 2016).*
International Search Report in PCT/AU2019/051195, dated Dec. 19, 2019.
Database GNPD [Online] Mintel; Aug. 1, 2014 [retrieved on Dec. 16, 2019], Philosophy, USA: "Instant Skin-Tone Perfecting Moisturizer SPF 20", Database accession No. 2582521.
Database GNPD [Online] Mintel; Sep. 1, 2012 [retrieved on Dec. 2, 2019], Niuer International Skin Lab, Taiwan: "Anti-Acne Sunscreen SPF 50/PA+++", Database accession No. 1887104.
Database GNPD [Online] Mintel; Nov. 1, 2016 [retrieved on Dec. 2, 2019], Gowoonsesang Cosmetics, South Korea: "Sensi-AC Sun Cream SPF 43 PA+++", Database accession No. 4326329.
Australian Government Department of Health, Therapeutic Goods Association. "Literature Review on the safety of titanium dioxide and zinc oxide nanoparticles in sunscreens" [online]. Version 1.1. Canberra, ACT: TGA, 2016 [retrieved on Dec. 16, 2019]. Chapter 2, p. 5, "Nanoparticle Characteristics."
Kabana ("What is the difference between titanium dioxide and zinc oxide?", an internet article (dated Aug. 21, 2008) obtained from the internet at: kabanaskincare.com/faqs/what-is-the-difference-between-titanium-dioxide-and-zinc-oxide/) (Year: 2008).
Antaria ("ZinClear™ The Natural Choice in Sun Care", an internet article (dated 2015) obtained from the World-Wide-Web at: deverauxspecialties.com/antaria/) (Year: 2015).
Chen, L.L. et al. 2013 "Nanotechnology in Photoprotection" Nanotechnology in Dermatology (Chapter 2), Eds Springer Science pp. 9-18.
International Search Report in International Application No. PCT/AU2018/050454, dated Aug. 9, 2018.
European Extended Search Report in European Application No. 19877765.8, dated Sep. 16, 2022.
Database WPI, Week 201555, Thomson Scientific, London, GB; AN 2015-43516F & CN 104 622 703 A (Wuxi Siyuan Cosmetics Co Ltd) May 20, 2015 (May 20, 2015).

* cited by examiner

*Primary Examiner* — Nannette Holloman
(74) *Attorney, Agent, or Firm* — Knobbe, Martens, Olson & Bear, LLP

(57) ABSTRACT

A composition for treating acne includes an anti-acne active agent that includes salicylic acid, an emulsifier, an emollient, particles of zinc oxide, water and a humectant. The composition has a sun protection factor (SPF) of at least 5. The zinc oxide can be included in a powder with particles that are formed as aggregates of smaller particles which, when used in a dispersion at a concentration of 50 weight % of zinc oxide, produces a transparent composition.

19 Claims, No Drawings

ANTI-ACNE COMPOSITION

TECHNICAL FIELD

The present invention relates to an anti-acne composition. More particularly, the present invention relates to an anti-acne composition having sunscreen properties or having a high sunscreen protection factor (SPF).

BACKGROUND ART

Acne can be a problem faced by many people, particularly during the teenage years. Acne is a condition where oil glands of the skin can become clogged, forming spots, pimples and sometimes cysts. Although acne is not a dangerous condition, it can lead to scarring of the skin. Further, because acne typically appears on the face, it can cause significant self-esteem issues, particularly in developing young adults.

There are a number of different acne treatments available. Acne treatments work in several different ways. Most aim to reduce the oiliness of the skin, unblock pores and/or reduce skin inflammation. Most common acne treatments are applied directly to the skin. These are known as topical treatments. In severe cases, oral medications may be prescribed by a doctor to treat severe acne.

Some topical acne treatments include keratolytics. These compositions are peeling agents that can be used to treat acne by unblocking skin pores. A number of these types of anti-acne compositions include salicylic acid as an active agent.

Other types of acne treatments include antibiotic agents or antibacterial agents. Benzoyl peroxide is widely used in these treatments. Other topical antibiotic preparations include the antibiotic clindamycin.

Retinoids are also used in acne treatment. These are very effective and work by unblocking skin pores, reducing the amount of oil that is produced by the sebaceous glands in the skin and reducing inflammation. These compounds can cause severe birth defects and therefore cannot be taken by pregnant women, those planning pregnancy or women who are not using appropriate contraceptive measures. These compositions work very effectively but can cause greater amounts of skin irritation than other topical acne compositions.

Acne compositions typically include a number of ingredients, with the active ingredients being fairly aggressive and reactive chemicals. As a result, changes to the compositions can cause unexpected effects.

A number of companies also sell sunscreen compositions that are promoted as being suitable for use by acne sufferers. There is a consensus that use of sunscreens will cause blockage of skin pores, which is likely to exacerbate acne. Some companies promote sunscreens that are oil free and will not clog pores, with these sunscreens being further promoted as being suitable for use by sufferers of acne.

It will be clearly understood that, if a prior art publication is referred to herein, this reference does not constitute an admission that the publication forms part of the common general knowledge in the art in Australia or in any other country.

SUMMARY OF INVENTION

The present invention is directed to a composition for treating acne, which may at least partially overcome at least one of the abovementioned disadvantages or provide the consumer with a useful or commercial choice.

With the foregoing in view, the present invention in one form, resides broadly in a composition for treating acne, the composition comprising an anti-acne active agent including salicylic acid, an emulsifier, an emollient, particles of zinc oxide, water and a humectant, the composition having a sun protection factor (SPF) of at least 5.

In one embodiment, the composition has an SPF of at least 15. In another embodiment, the composition has an SPF of 30 or more.

In one embodiment, the composition further includes a salt. In one embodiment, the composition further includes a preservative.

In one embodiment, the particles of zinc oxide are sized less than 1 μm.

The zinc oxide that is present in the composition may be in the form of fine particles. The zinc oxide may comprise the product sold by Antaria Pty Ltd under the trade name ZinClear XP and/or ZinClear XP dispersions and/or ZinClear XP 65COCO. These products may be as described in Australian patent number 2009203996 and in international patent publication number WO 2009/089523, the entire contents of which are herein incorporated by cross-reference. The zinc oxide particles may also be the same as the zinc oxide particles used in the sunscreen composition described in Australian patent number 2003205436, the entire contents of which are herein incorporated by cross-reference.

In one embodiment, the zinc oxide comprises ZinClear XP 65COCO and ZinClear XP.

In some embodiments, the zinc oxide may be in the form of aggregates of primary particles.

ZinClear XP comprises zinc oxide particles that are formed as aggregates of smaller particles. As described in Australian patent number 2009203996, ZinClear XP is a zinc oxide powder comprising zinc oxide agglomerates which, when used in a dispersion at a concentration of 50 weight % of zinc oxide, produces a transparent composition having a total visible transmittance through a path length of 20 μm at 550 nm of at least 70%, the powder having a number average zinc oxide aggregate size of at least 0.8 μm, wherein the aggregates are mesoporous and have a total mesopore volume of at least 0.25 $cm^3$ per gram. High-energy milling of ZinClear XP can break up the zinc oxide aggregates to reduce the overall particle size of the aggregates. ZinClear XP comprises 99 to 100% zinc oxide.

ZinClear XP 65COCO is a mixture of zinc oxide (in the form of ZinClear XP), coco-caprylate/caprate, polygylceryl-3 polyricinoleate and isostearic acid. It is a commercially available product can be purchased from Antaria Pty Ltd. ZinClear XP 65COCO is a dispersion that includes coco-caprylate/caprate as an emollient. It has high transparency and low whiteness. ZinClear XP 65COCO contains 65% zinc oxide.

In one embodiment, the composition comprises from 22 to 28% by weight zinc oxide, or from 23 to 27% by weight zinc oxide, or from 24 to 26% by weight zinc oxide, or about 25% by weight zinc oxide.

In one embodiment, the composition has from 33.8 to 43.1% by weight ZinClear XP 65COCO, or from 35.3 to 41.5% by weight ZinClear XP 65COCO, or from 36.9 to 39.9% by weight ZinClear XP 65COCO, or about 38.50% by weight ZinClear XP 65COCO.

Throughout this specification, all percentages of ingredients are given on the basis of a weight percentage based on the final composition. For example, if one ingredient is present in an amount of 15%, there will be 15 g of that ingredient in 100 g of the final composition.

In one embodiment, the anti-acne agent comprises salicylic acid. In another embodiment, the anti-acne active agent comprises salicylic acid and a *Magnolia Officinalis* bark extract. The *Magnolia Officinalis* bark extract has anti-acne and antimicrobial effects. The *Magnolia Officinalis* bark extract may be commercially purchased from a German company Cosphatec under the trade name Cosphaderm Magnolia Extract 98.

In one embodiment, the composition comprises from 0.35 to 0.65 weight percent salicylic acid.

In some instances, the composition may include a preservative, with the preservative including salicylic acid. In those embodiments, the salicylic acid arising from the preservative is in addition to the amount of salicylic acid set out above.

In one embodiment, the composition comprises of a mixture of excipients that provide humectant, preservative, salting and emollient functions. The combination of these excipients may be present in an amount of from 5% to 10% by weight.

In one embodiment, the emulsifier may be present in an amount of from 5 to 10% by weight, or in an amount of from 6 to 9% by weight, or in an amount of from 7 to 8% by weight, or about 7.50% by weight. The emulsifier may comprise Symbiomuls WO-AF, available from Evonik Dr. Straetmans GmbH. This product is an emulsifier blend for water/oil emulsions with a synergistic mixture of emulsifiers, waxes and stabilisers, and is free of aluminium compounds. Other emulsifiers may be used.

An emollient is added to soften or soothe the skin. The emollient may be present in an amount of from 6 to 10% by weight, or from 7 to 9% by weight, or about 8% by weight. Any suitable emollient may be used, with jojoba oil being one example.

The composition further comprises water. The water is suitably demineralised water. The water may be present in an amount of from 35 to 40% by weight, or from 36 to 39% by weight, or from 36 to 38% by weight, or about 37% by weight.

The present invention also relates to a method for preparing an anti-acne composition. Accordingly, in a second aspect, the present invention provides a method for preparing an anti-acne composition, the composition comprising an anti-acne active agent including salicylic acid, an emulsifier, an emollient, particles of zinc oxide, water and a humectant, the method comprising
a) combining the anti-acne agent, the emollient and the emulsifier and mixing at an elevated temperature to obtain a homogenous mixture,
b) adding the particles of zinc oxide to the mixture from step (a) and stirring to obtain a mixture,
c) mixing water and the humectant and adding the water and humectant to the mixture from step (b) with stirring, and
d) cooling to room temperature whilst maintaining stirring.

In one embodiment, step (a) is conducted a temperature of from 70° C. to 90° C., or from 80° C. to 85° C.

Steps (b) and (c) may be conducted at the same temperature as a step (b). In other words, the temperature of the mixture is maintained during steps (c) and (d).

In one embodiment, salt and preservative are mixed with the humectant and that mixture is subsequently mixed with water in step (c).

Step (b) may involve adding the particles of zinc oxide to the mixture from step (a) under vigorous stirring.

In some embodiments, step (c) may involve very slowly adding the mixture of water and humectant (and optionally salt and preservative) to the mixture from step (b).

In some embodiments, the mixture of all ingredients resulting from step (c) is homogenised by further mixing to obtain a homogenous mixture.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

DESCRIPTION OF EMBODIMENTS

A composition was made from the following ingredients:

| Phase | INCI Name | % w/w | Function |
|---|---|---|---|
| A | Polyglyceryl-3 Polyricinoleate (and) Sorbitan Sesquioleate (and) Cetyl Ricinoleate (and) Glyceryl Caprate (and) Cera Alba (and) Magnesium Stearate | 7.50 | Emulsifier |
|   | *Simmondsia Chinensis* (Jojoba) Seed Oil | 8.00 | Emollient |
|   | Salicylic Acid | 0.20-0.90 | |
| B | Zinc Oxide (and) Coco-Caprylate/Caprate (and) Polyglyceryl-3 Polyricinoleate (and) Isostearic Acid | 38.50 | Inorganic UV Filter |
| C | Water | 37.00 | |

The composition was prepared by combining a sensory modifier, anti-microbial agent and salicylic acid to an amount less than 4% by weight, with the ingredients of phase A. The combining ingredients were heated to 80-85° C. with stirring until all components were molten/dissolved. Phase B was added to the phase A mixture with vigorous stirring, whilst maintaining temperature. The humectant, preservatives and salt were mixed together to an amount less than 6% by weight. Water was added to that mixture with stirring until all components were fully dissolved to form phase C. Phase C was very slowly added to the mixture of phases A and B with intensive stirring, whilst maintaining temperature. The resulting mixture was then homogenised for one minute per 100 g of mixture. The mixture was cooled to room temperature whilst undergoing vigorous stirring during cooling.

The composition set out above was tested and found to have an SPF of at least 30. It is expected that the composition will demonstrate effective treatment of acne in a number of patients.

The present inventors are not aware of any existing anti-acne compositions that have a high SPF factor and can therefore also function as a sunscreen. Indeed, conventional thinking in this art is that sunscreens exacerbate acne because sunscreen tends to block the pores of the skin. In contrast, most medical practitioners believe that the pores of the skin should be cleared in order to properly treat acne. Further, anti-acne compositions typically contain a number of quite aggressive chemicals and the interaction of those chemicals with other compounds can be unpredictable. Indeed, the present inventors took in excess of 2 years of experimentation to arrive at a composition that is effective in treating acne, has a good SPF rating and is stable with a reasonable shelf life.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A composition for treating acne, the composition comprising an anti-acne active agent including from 0.35 to 0.65 weight percent salicylic acid, an emulsifier, an emollient, particles of zinc oxide, the particles of zinc oxide being present in an amount of from 22 to 28% by weight, water and a humectant, the composition having a sun protection factor (SPF) of at least 30, wherein the composition includes a mixture of zinc oxide, coco-caprylate/caprate, polyglyceryl-3 polyricinoleate and isostearic acid, and wherein the water is present in an amount of from 35 to 40% by weight.

2. A composition as claimed in claim 1 wherein the composition has an SPF of at least 50.

3. A composition as claimed in claim 1, wherein the composition further includes a salt and/or a preservative.

4. A composition as claimed in claim 1, wherein the particles of zinc oxide are sized less than 1 µm.

5. A composition as claimed in claim 1, wherein the zinc oxide are in the form of aggregates of primary particles.

6. A composition as claimed in claim 1, wherein the composition comprises a powder comprising zinc oxide particles that are formed as aggregates of smaller particles which, when used in a dispersion at a concentration of 50 weight % of zinc oxide, produces a transparent composition having a total visible transmittance through a path length of 20 µm at 550 nm of at least 70%, the powder having a number average zinc oxide aggregate size of at least 0.8 µm, wherein the aggregates are mesoporous and have a total mesopore volume of at least 0.25 cm$^3$ per gram.

7. A composition as claimed in claim 1, wherein the composition comprises from 23 to 27% by weight zinc oxide.

8. A composition as claimed in claim 1, wherein the anti-acne active agent comprises salicylic acid and a *Magnolia Officinalis* bark extract.

9. A composition as claimed in claim 1, wherein the composition comprises of a mixture of excipients that provide humectant, preservative, salting and emollient functions, the combination of these excipients being present in an amount of from 5% to 10% by weight.

10. A composition as claimed in claim 1, wherein the emulsifier is present in an amount of from 5 to 10% by weight.

11. A composition as claimed in claim 1, wherein the emollient is present in an amount of from 6 to 10% by weight.

12. A composition as claimed in claim 1, wherein the water is demineralized water.

13. A method for preparing an anti-acne composition according to claim 1, the method comprising
   a) combining the anti-acne agent, the emollient and the emulsifier and mixing at an elevated temperature to obtain a homogenous mixture,
   b) adding the particles of zinc oxide to the mixture from step (a) and stirring to obtain a mixture,
   c) mixing water and the humectant and adding the water and humectant to the mixture from step (b) with stirring, and
   d) cooling to room temperature whilst maintaining stirring.

14. A method as claimed in claim 13, wherein step (a) is conducted a temperature of from 70° C. to 90° C.

15. A method as claimed in claim 13, wherein steps (b) and (c) are conducted at the same temperature as a step (b).

16. A method as claimed in claim 13, wherein salt and preservative are mixed with the humectant and that mixture is subsequently mixed with water in step (c).

17. A method as claimed in claim 13, wherein step (b) comprises adding the particles of zinc oxide to the mixture from step (a) under vigorous stirring.

18. A method as claimed in claim 13, whereon step (c) comprises very slowly adding the mixture of water and humectant and optionally salt and preservative to the mixture from step (b).

19. A method as claimed in claim 13, wherein the mixture of all ingredients resulting from step (c) is homogenized by further mixing to obtain a homogenous mixture.

* * * * *

UNITED STATES PATENT AND TRADEMARK OFFICE
CERTIFICATE OF CORRECTION

| | |
|---|---|
| PATENT NO. | : 11,872,297 B2 |
| APPLICATION NO. | : 17/290165 |
| DATED | : January 16, 2024 |
| INVENTOR(S) | : Julian Hewitt |

It is certified that error appears in the above-identified patent and that said Letters Patent is hereby corrected as shown below:

On the Title Page

Column 1 item (71) (Applicant), Line 1, delete "Advance NanoTek Ltd.," and insert -- Advance Zinctek Limited, --.

In the Specification

At Column 2, Lines 49-50, delete "polygylceryl" and insert -- polyglyceryl --.

Signed and Sealed this
Tenth Day of December, 2024

Katherine Kelly Vidal
*Director of the United States Patent and Trademark Office*